United States Patent [19]

Zolle

[11] 3,937,668

[45] Feb. 10, 1976

[54] METHOD FOR INCORPORATING SUBSTANCES INTO PROTEIN MICROSPHERES

[76] Inventor: Ilse Zolle, Lazarettgasse 14A, Vienna 1090, Austria

[22] Filed: Nov. 6, 1972

[21] Appl. No.: 304,218

Related U.S. Application Data

[63] Continuation-in-part of Ser. No. 55,231, July 15, 1970, abandoned.

[52] U.S. Cl. ............... 252/316; 427/3; 252/301.1 R; 252/301.1 S; 252/408; 264/.5; 424/1; 424/2; 424/7; 424/19; 424/36; 424/178
[51] Int. Cl. ........................ B01j 13/02; B44d 1/02
[58] Field of Search .......... 252/316, 301.1 R; 424/1, 424/2, 36, 37, 19, 178; 264/.5; 117/100 A

[56] References Cited
UNITED STATES PATENTS

| | | | |
|---|---|---|---|
| 2,911,338 | 11/1959 | Tabern et al. | 424/1 |
| 3,137,630 | 6/1964 | Hecker et al. | 264/14 |
| 3,137,631 | 6/1964 | Soloway | 252/316 X |
| 3,663,685 | 5/1972 | Evans | 424/1 |

FOREIGN PATENTS OR APPLICATIONS

| | | | |
|---|---|---|---|
| 310,934 | 12/1930 | United Kingdom | 424/178 |

*Primary Examiner*—Richard D. Lovering

[57] ABSTRACT

The subject matter of this invention is a process for solid albumin particles so that such spheric particles may act as a carrier for radioactivity, drugs, insecticides, dyes, metal salts, etc. In order to prepare such spheric particles, the substance to be incorporated therein is transformed into a precipitate. This precipitate is then mixed with an aqueous solution of albumin. The mixture thus prepared is then injected into cotton seed oil while stirring so as to obtain a fine dispersion of the albumin droplets and the precipitate in the oil, then the mixture is heated above 100°C to evaporate water and to form spheric albumin particles having the precipitate encapsulated therein.

1 Claim, No Drawings

METHOD FOR INCORPORATING SUBSTANCES INTO PROTEIN MICROSPHERES

This application is a continuation-in-part of Ser. No. 55,231 filed July 15, 1970 now abandoned.

Encapsulation of various substances as solids or liquids into proteins, such as gelatin or albumin has been known. Solid gel capsules having a medicine dispersed therein, or partially gelled or denatured or coagulated capsules containing a liquid with a medicine have been described (British Pat. No. 795,977). These capsules are made of swellable colloid and are fragile and, depending on their pore size, permeable for liquids. They can be hardened, but are then not suitable for parenteral use. Water insoluble organic liquids have been incorporated into solid protein shells, denatured by heat. (U.S. Pat. No. 3,137,631, 1964). They could be prepared from protein alone, but increased stability was accomplished by the addition of cross-linking agents for the proteins. The particles obtained by either process are however always fragile, unless specifically hardened, and contain usually a liquid core within a thin protein shell. They are difficult to obtain in homogenous sizes around 50 microns and are difficult to store. Because of their fragility, and antigenicity (if hardened) they cannot be used parenterally in animal or man.

Depending on the type of substance that one wants to incorporate and on the type of product one wants to obtain, one has to use the proper method for incorporation or encapsulation. The methods used by the British and U.S. patents are useful for the preparation of gelled particles at temperatures below 100°C. Hard, solid albumin spheres may be obtained by dispersion and subsequent heating of an albumin solution (25%) in oil. These particles are obtained as a dry, free flowing powder consisting of spheric particles of albumin.

It is known that spheric particles of protein or starch and possibly of other materials may be obtained when a concentrated aqueous solution of the protein or the starch is mixed with another liquid not miscible with water. This liquid may be an organic solvent or an oil or a more concentrated solution of a salt. In the preferred embodiment of the invention a 25% solution of albumin (human serum albumin), generally referred to as HSA, and cotton seed oil will be used because HSA has well known biological properties useful in biological labeling.

There is a great interest in medicine for spheric particles made of a degradable material, which can withstand arterial pressure systems after being injected. Presently used aggregates of albumin labelled with I-131 are too fragile. Therefore there is great need in the art for methods permitting the use of spherical albumin particles as a carrier for radioactivity, dyes and medicines. The invention to be hereinafter described fulfills this need.

In order to incorporate radioactivity, a medicine or any substance into said albumin particles, the substance to be incorporated is transformed into a precipitate for incorporation. This offers the advantage that a substance or a chemical element which is present in a large volume may be concentrated into a few milligrams of precipitate which can be easily incorporated into albumin spheres. A solid, which is coarse and not available in homogenously sized crystals, may be dissolved and precipitated as another chemical compound and as such may be homogenously incorporated into albumin spheres. A substance strongly acidic or alkaline, which would interfere with the particle preparation when added to the albumin solution, would be extracted from such environment and incorporated as a neutral precipitate. It should be emphasized that the incorporation of liquids into solid albumin spheres is not meaningful, because liquids evaporate during the heating step above 100°C and besides, only small volumes of a solution can be added to the 25% albumin solution, so as not to cause too much dilution. In addition it may be mentioned that the incorporation of a radioactive solution resulted in albumin particles, which released up to 50% of the incorporated radioactivity when suspended in the injection medium (physiological saline). A tight fixation of radioactivity, which is essential for parenterally used albumin spheres is obtained when a precipitate of the radionuclide is incorporated. Radionuclides are mostly supplied as solutions. In order to accomplish incorporation, chemical precipitation into a water insoluble precipitate is performed. In general there are the following methods for incorporation or fixation of a substance into solid albumin spheres:

1. Fixation of a radionuclide:
   Direct labelling of the albumin matrix of the particles by the known labelling reactions for albumin (with Tc-99m: Stern H. S., Zolle I., J. G. McAfee, Int. J. Appl. Rad. & Isotopes 16:283, 1965, with iodine: Hunter W. M., In Radioactive Pharmaceuticals, ABC Symposium Series 6, U.S. Atomic Energy Comm., Div. of Techn. Inf., Springfield, Va. (1966):245)

2. Fixation of the radionuclide via another chemical element or carrier which has been incorporated into the albumin matrix: i.e. incorporation of ferric-hydroxide precipitate into albumin particles facilitates labelling of the finished albumin spheres with Tc-99m and In-113m (with Tc-99m: I. Zolle, B. A. Rhodes, H. N. Wagner, Jr., J. Appl. Rad. & Isotopes 21, 155, 1970; with In-113m: J. W. Buchanan, B. A. Rhodes, H. N. Wagner, Jr., J. Nucl. Med. 10, No. 7:487, 1969)

3. Incorporation of a medicine: Insulin, available as a solution 20/mg/ml) is transformed into an amorphous precipitate and thus albumin particles containing insulin are obtained. Crystalline insulin may not be incorporated as homogenously.

Incorporation of dry salts or powdered substances is possible; however, certain chemical salts react with the albumin and cause coagulation of the albumin, so that preparation of spheres is no longer possible. It is important that the albumin maintains its physiological properties. If the salts are dissolved and precipitated as a neutral precipitate, incorporation of the desired element into solid albumin spheres can be accomplished. Precipitation may be brought about in several ways, depending on the chemical nature of the substance. The precipitate is then mixed with the aqueous solution of the protein or the starch and this homogenous mixture is dispersed in the non-miscible phase, preferably cotton seed oil, for sphere formation. Because of immiscibility, the precipitated substance remains in the aqueous protein (i.e. HSA)-phase and becomes encapsulated in the albumin spheres.

As is generally known HSA microspheres may be prepared in the following way. One half milliliter of a 10–30 percent solution of HSA is injected into 120 ml. of cotton seed oil (USP) while stirring. After a fine dispersion of the HSA is obtained in the oil, (after 5 min.), heating above 100°C is started to evaporate the water and thus to solidify the fragile albumin droplets. After heating is completed, usually within 45 minutes, the protein spheres are centrifuged from the oil and washed with ether. This way one obtains spheric particles between 1 micron and 200 microns, depending on the speed of stirring.

Radionuclides may be incorporated into solid HSA particles by using the invention in the following way. Radio-nuclides are generally available in solutions. Therefore, to precipitate the radionuclide it is necessary to adjust the volume to a convenient amount for precipitation and the pH to the point where precipitation is to occur. Precipitation is then brought about by addition of stoichiometric amounts of that reagent, which is necessary to form the precipitate. After precipitation is complete, the sample is centrifuged and the precipitate washed with water. After the last wash (if several washings are performed) the water is removed almost completely and the precipitate may be incorporated into the 25% albumin solution as such. If necessary, larger aggregates may be redispersed by addition of a peptizing electrolyte or by ozonification of the precipitate. The radionuclide precipitate is then mixed with the HSA solution and then the mixture is injected into cotton seed oil as previously described. This process results in the creation of spheric HSA particles incorporating radionuclide.

For example, radioiodide may be incorporated into HSA spheres in the following way. The radionuclide is precipitated from slightly acidic (pH 6) solutions with stoichiometric amounts of 0.1 M (molar) silver nitrate solution. Since radio-iodide is obtained in strongly alkaline solutions of pH 11–13, it is necessary to adjust the pH before silver nitrate is added. When carrier free radioiodide is used, 10 mg. of potassium iodide (KI) is added as a carrier prior to precipitation. In order to ensure complete precipitation of the radionuclide, the pH is adjusted to 9.5. Then the precipitate is separated by centrifugation and washed twice with water.

For example, 5mCi of $^{123}I$ were obtained in 11 ml alkaline solution at pH 13.0. After pH adjustment to pH 6.0, 1.2 ml of 0.1 M silver nitrate solution was added and the pH adjusted to 9.5 to facilitate complete precipitation. The amount of silver nitrate solution had to be estimated, as the amount of carrier originally present in the $^{123}I$ solution was unknown. When insufficient silver nitrate was added, the supernatant remained opalescent and contained considerable amounts of the radioactivity; dropwise addition of silver nitrate solution completed the precipitation, a slight excess of silver nitrate being indicated by the appearance of brown silver oxide.

In the same manner radioactive chromium can be incorporated into HSA particles. Chromium 51 is available as chromic chloride and as sodium chromate solution. Chromates may be precipitated directly by the addition of silver nitrate solution while chromic chloride needs to be oxydized to chromate before precipitation. 10 mg of potassium chromate ($K_2CrO_4$) carrier may be added to the solution of the radioactive chromium (51) before the precipitation with stoichiometric amounts of 0.1 M silver nitrate solution at neutral pH. The precipitate is red brown and is washed with water, which is removed carefully before addition of the peptizing electrolyte. It is then added to the HSA solution and mixed with cotton seed oil as previously described.

Inorganic salts may also be incorporated into HSA particles using the invention. Some inorganic salts (i.e. ferrous sulfate) cause coagulation of the protein, (i.e. albumin) when the salt is directly added to the 25% albumin solution for incorporation into albumin spheres. This can be avoided by precipitation of the ferrous sulfate as the hydroxyde, which is insoluble in water and does not cause coagulation of the albumin and can therefore be incorporated into albumin spheres without difficulties using the techniques previously described. In addition, freshly precipitated ferric hydroxyde is homogeneously distributed within the spheres by this method of incorporation. Inorganic salts may be incorporated to facilitate chemical reactions performed with the finished spheres.

If ferric hydroxyde is incorporated into spheres, these spheres become more reactive for a certain labeling procedure with Technetium 99m, a very useful radionuclide in diagnostic and investigative medicine. Spheres can be prepared in advance and stored and labeled just prior to use by a very simple and efficient technique developed for ferric hydroxyde containing albumin spheres. Ferric ion lends itself to a variety of reactions such as the Prussian Blue reaction, which may be used to prepare intensively blue particles, when this might be of advantage.

Ferric or ferrous hydroxyde may be precipitated from its chloride solutions by the addition of 0.1 M sodium hydroxyde solution till precipitation is complete. This is usually around pH 5. The precipitate is separated by centrifugation and washed with water. Then it may be redispersed by addition of ferric chloride or by ozonification.

Further, for incorporation into HSA microspheres, a precipitate should consist of homogeneously sized crystals, so that the nuclide is distributed evenly within the microspheres. Many precipitates tend to form larger aggregates with time; silver iodide crystals form larger aggregates within seconds after precipitation. To redisperse such large aggregates, salts can be added which act as peptizing electrolytes. Small traces of specific electrolytes, which are often necessary to obtain stable sols, are in several cases also capable of redispersing a precipitate to a sol.

In the case of silver iodide precipitates, potassium iodide may be added; in the case of ferric hydroxide precipitates, ferric chloride may be used. Only small volumes of the peptizing electrolytes ranging from 2–10 ml were added to the washed precipitates while stirring. This was necessary to avoid dilution of the precipitates, and also to avoid changes in the pH of the precipitates. For redispersion of ferric hydroxide obtained with 30 mg ferric chloride, only 2 ml of a solution containing 400 mg of ferric chloride/ml water could be used (0.8 mg), because of the acidity of the ferric chloride solution, coagulation of the HSA solution resulted when added to the precipitate. Redispersed precipitates were mixed with 0.5 ml of the 25% HSA solution and microspheres prepared as described above.

Three types of silver iodide precipitates have been incorporated into HSA microspheres: (1) silver iodide precipitates (obtained with 10 mg KI carrier) that had not been redispersed. Microspheres showed uneven distribution of the precipitate or inclusions of larger silver iodide crystals within the microspheres; (2) silver iodide precipitate that had been redispersed with the addition of 10% KI as peptizing electrolyte. Based on the amount of KI carrier, this was 10 ml of a solution of 100 mg of KI/ml. Microspheres showed even distribution of the precipitate with few bigger crystals of silver iodide within the microspheres; (3) silver iodide precipitate that had been redispersed with addition of 20% KI as peptizing electrolyte (10 ml of a solution of 200 mg of KI/ml). Microspheres showed a homogeneous distribution of silver iodide precipitate within the microspheres.

It was observed that aggregates of AgI crystals were partially redispersed with less than 10% KI. However, when more that 10% KI was added, dispersion proceeded into colloidal ranges, indicated by a relatively high percentage of free radioactivity in the suspension medium. An addition of 10% peptizing electrolyte gave a very homogeneous distribution of the silver iodide precipitate within the microspheres and only small amounts of free radioactivity in the injection medium.

Other proteins may also be incorporated into HSA microspheres. A protein may be obtained as a precipitate at its isoelectric point. Any protein present in an aqueous solution may be transformed into a precipitate by adjustment of the pH to the value of its isoelectric point. Most proteins form amorphous precipitates. These are most suitable for incorporation into albumin spheres, because they are distributed evenly within the spheres. No peptizing electrolytes are needed to redisperse large aggregates.

For example, commercially available insulin (Iletin, 500 Units/ml/20mg) may be used for precipitation at pH 5.6 in the presence of sodium citrate and zinc chloride.

Various amounts of insulin may be incorporated, one will aim to incorporate as much insulin as possible, if these spheres should be used for insulin therapy, as with increasing amounts of albumin the units of biologically active insulin released per mg of spheres decrease. The example will demonstrate the incorporation of 84% of insulin using 16% of albumin for the preparation of spheres:

- 7.68 ml insulin (Iletin)
- 0.07 ml sodium citrate solution (0.05 M, pH 7.8)
- 0.77 ml zinc chloride (1 mg/ml) = 0.5%
- 0.1 ml $I^{125}$-labeled insulin (only required, when radiometric measurements are performed for quantification)
- 2.73 ml sodium citrate solution (0.05 M, pH 7.8)

The pH of the mixture is 5.6 for maximal precipitation of the insulin.

The precipitate is centrifuged and washed with distilled water. All water is carefully removed. The volume of the precipitate is large, approximately 3 ml. 0.1 ml of albumin solution (300 mg/ml) is added. While stirring, the mixture is injected into cotton seed oil for the preparation of insulin containing albumin spheres. The insulin spheres showed more than 85% incorporation of insulin measured by the simultaneous incorporation of $I^{125}$-labeled insulin and less than 1% free insulin when suspended in saline.

The insulin retained its biological activity measured by the decrease of blood sugar levels in dogs.

The incorporation of biologically active substances may serve the purpose of sustained release of the incorporated drug from the spheres as the spheres slowly dissolve in the biological system.

The procedure described for the preparation of spheres between 1–200 microns may be modified so that spheres of 1 micron and smaller can be prepared.

Spheric particles in very homogenous size distribution around 1 micron are prepared if the 25% albumin solution with the precipitate of the substance to be incorporated and the cotton seed oil together are pressed through a fine capillary or rotating disc. In the laboratory a handhomogenizer, Logeman, U.S. Pat. No. 2,064,402, is used, for large scale preparations, pharmaceutical homogenizers used for the preparation of emulsions, may be used. This way an emulsion of the aqueous albumin is obtained in the oil indicating an extremely fine dispersion of the droplets in the oil. Heating of the emulsion is performed for 10 min. by pouring the prepared emulsion into preheated oil of 200°C. The water evaporates immediately leaving solid millimicrospheres in the oil. After cooling, diethylether is added to break the emulsion and the millimicrospheres are separated from the organic phase by centrifugation. Millimicrospheres may be well suspended with the aid of a suspending agent (such as Tween 80, USP) and labelled with radionuclides according to the known procedures. Ferrichydroxide precipitate may also be incorporated and labelling with Tc-99m performed as described for albumin. Labelled millimicrospheres localize in the phagocytic cells of the reticulo-endothelial system, when injected intravenously, while the albumin spheres between 5 and 60 microns as described previously, are retained by the lung capillaries. Thus the larger particles may be used for blood flow distribution measurements, while millimicrospheres present a novel agent for the measurement of the phagocytic capacity of the reticuloendothelial system.

Thus, it has been shown that various distinct types of substances may be incorporated into albumin microspheres by the process of precipitating out the substance and then incorporating said precipitate in the aqueous solution of albumin before the albumin microspheres are prepared in the manner previously described, which is by injecting said mixture into a liquid immiscible with water, heating above 100°C and then separating the spheres formed therein from the immiscible liquid. However, the advantages offered by the described technique, namely the incorporation of precipitates into spheric albumin particles, may as well be applied for a tight fixation of any substance within gel particles prepared below 100°C, which are described in the British Patent. The permeable, porous membrane of these capsules allows incorporated liquids to leak out, yet precipitates may not pass. In addition, concentration of the substance from a large volume, which is too large to be incorporated into a few milligrams of precipitate which can easily be enclosed, is an important advantage. As indicated initially, spheric particles may not only be obtained from protein solutions, but also polysaccharides, such as starch or glycogen may be used as the spheric matrix. If these particles are used as a carrier for radionuclides, drugs, metal salts, dyes or medicines, fixation or incorporation of a precipitate of the radionuclide, the drug or the metal salt (as a chemical carrier for subsequent labelling with radionuclides or to produce a color reaction) or the medicine may be accomplished using the described invention.

The embodiments of the invention in which an exclusive property or privilege is claimed are defined as follows:

1. A process for incorporating a substance capable of being precipitated into albumin millimicrospheres comprising: preparing a precipitate of said substance and forming a mixture of the precipitate with an aqueous solution of albumin; injecting said mixture into oil and pressing the resultant through a fine capillary or rotating disc to form an extremely fine emulsion of droplets of the precipitate and albumin in said oil, heating said oily mixture above 100°C and separating the formed albumin millimicrospheres from said oil having said precipitate encapsulated therein.

* * *